United States Patent [19]
Kilmer et al.

[11] Patent Number: 5,318,044
[45] Date of Patent: Jun. 7, 1994

[54] METHOD AND APPARATUS FOR RE-PROFILING THE CORNEA TO CORRECT FOR HYPEROPIA

[75] Inventors: Lauren G. Kilmer; Alvin E. Reynolds, both of Tulsa, Okla.

[73] Assignee: Corneal Contouring, Inc., Azusa, Calif.

[21] Appl. No.: 762,866

[22] Filed: Sep. 18, 1991

Related U.S. Application Data

[63] Continuation-in-part of Ser. No. 450,672, Dec. 14, 1989, Pat. No. 5,063,942, and a continuation-in-part of Ser. No. 939,856, Sep. 2, 1992, which is a continuation of Ser. No. 894,162, Jun. 3, 1992, abandoned, which is a continuation of Ser. No. 592,601, Oct. 4, 1990, abandoned.

[51] Int. Cl.$^5$ ............................................. A61F 9/00
[52] U.S. Cl. ........................................ 128/898; 606/161; 606/166
[58] Field of Search ............ 606/161, 166, 167, 5, 606/4, 180; 604/22; 128/898, 751, 757, 755

[56] References Cited

U.S. PATENT DOCUMENTS

| | | | |
|---|---|---|---|
| 2,249,906 | 7/1941 | Longoria | 128/305 |
| 2,480,737 | 8/1949 | Jayle | 128/305 |
| 3,172,404 | 3/1965 | Copenhaver | 128/2.1 |
| 3,976,077 | 8/1976 | Kerfoot, Jr. | 128/305 |
| 4,173,980 | 11/1979 | Curtin | 128/303 |
| 4,205,682 | 6/1980 | Crock et al. | 606/166 |
| 4,381,007 | 4/1983 | Doss | 128/303 |
| 4,423,728 | 1/1984 | Lieberman | 128/310 |
| 4,526,171 | 7/1985 | Schachar | 128/305 |
| 4,619,259 | 10/1986 | Graybill | 128/305 |
| 4,665,913 | 5/1987 | L'Esperance, Jr. | 128/303 |
| 4,688,570 | 8/1987 | Kramer et al. | 606/166 |
| 4,718,418 | 1/1988 | L'Esperance, Jr. | 128/303 |
| 4,724,522 | 2/1988 | Belgorod | 364/415 |
| 4,729,372 | 3/1988 | L'Esperance, Jr. | 128/303.1 |
| 4,744,362 | 5/1988 | Grundler | 606/166 |
| 4,750,491 | 6/1988 | Kaufman | 128/305 |
| 4,763,651 | 8/1988 | Kaufman | 128/310 |
| 4,770,172 | 9/1988 | L'Esperance, Jr. | 128/303 |
| 4,798,204 | 1/1989 | L'Esperance, Jr. | 128/303 |
| 4,834,748 | 5/1989 | McDonald | 623/5 |
| 4,838,266 | 6/1989 | Koziol | 128/303.1 |
| 4,840,175 | 6/1989 | Peyman | 128/303.1 |
| 4,947,871 | 8/1990 | Grieshaber | 128/898 |
| 5,063,942 | 11/1991 | Kilmer et al. | 606/161 |

FOREIGN PATENT DOCUMENTS

| | | | |
|---|---|---|---|
| 303174 | 2/1989 | European Pat. Off. | 606/166 |
| 3433581 | 3/1986 | Fed. Rep. of Germany | 606/166 |
| 2595243 | 9/1987 | France | 606/166 |

OTHER PUBLICATIONS

Mueller, et al Expil Eye Res. (1967)6, 42–47 pp. 42–50 Some Experiments on Corneal Grinding.
Straatsma, et al Arch Ophthal-vol. 88, Sep. 1972 pp. 325–329 Stereotaxic Intraocular Surgery.

Primary Examiner—Edgar S. Burr
Assistant Examiner—Christopher A. Bennett
Attorney, Agent, or Firm—Head & Johnson

[57] ABSTRACT

Hyperopia (far-sighted) refractive error of the cornea is corrected by a scraping procedure of rotating or oscillating a tool having a central pressure pad with a plurality of curved sharpened knife-edge blades that initially are tangential to and against an outer zone or band of the cornea and micro-axially advanced until the refractive error has been corrected.

31 Claims, 5 Drawing Sheets

METHOD AND APPARATUS FOR RE-PROFILING THE CORNEA TO CORRECT FOR HYPEROPIA

This application is a continuation-in-part of Ser. No. 07/450,672, filed Dec. 14, 1989 now U.S. Pat. No. 5,063,942; and Ser. No. 07/939,856 filed Sep. 2, 1992 which is a file wrapper continuation of Ser. No. 894,162 filed Jun. 3, 1992, now abandoned, which is a file wrapper continuation of Ser. No. 592,601 filed Oct. 4, 1990 and now abandoned.

BACKGROUND OF THE INVENTION

This invention relates to a method and apparatus for adjusting the shape of components of the eye and more particularly to making fixed changes in the corneal curvature.

Deviations from the normal shape of the corneal surface produce errors of refraction in the visual process. The eye in a state of rest, without accommodation, focuses the image of distant objects exactly on the retina. Such an eye enjoys distinct vision for distant objects without effort. Any variation from this standard constitutes ametropia, a condition in which the eye at rest is unable to focus the image of a distant object on the retina. Hyperopia, or far-sightedness, is an error of refraction in which, with the eye at rest, parallel rays from distant objects are brought to focus behind the retina. Divergent rays from near objects are focused still further back. In one aspect of hyperopia, the corneal surface is flattened which decreases the angle of refraction of rays as they pass through the refractive surfaces of the cornea, causing a convergence or focus of the rays at a point behind the retina. The retina is comprised partially of nerve fibers which are an expansion of the optic nerve. Waves of light falling on the retina are converted into nerve impulses and carried by the optic nerve to the brain to produce the sensation of light. To focus parallel rays on the retina, the hyperopic eye must either accommodate, i.e., increase the convexity of its lens, or a convex lens of sufficient strength to focus rays on the retina must be placed before the eye.

The normal treatment of these classic forms of refractive error of the eye is with the use of eyeglasses or contact lenses, both of which have well-known disadvantages to the user. Recent research has been directed to operative techniques to change the refractive condition of the eye. Such techniques are generally referred to as "keratorefractive techniques". Two such techniques are more particularly called keratophakia and keratomileusis. Keralomileusis involves the regrinding of a corneal lamella into a meniscus or hyperopic lens to correct myopia or hyperopia. A corneal optical lathe has been especially developed for this procedure and is also used in the keratophakia procedure, when a homograft ground into a convex lens is placed interlamellarly to correct aphakic hypermetropia. The homograft tissue (corneal lamella) is frozen with carbon dioxide. The homograft is cut as a contact lens would be, i.e., to the optical power required to effect the desired optical correction of the cornea. In keratomileusis, the anterior corneal lamella is shaped by the lathe and in keratophobia, it is the corneal stroma of a donor eye that is shaped by the lathe. These techniques have a broad application in the correction of high hyperopic and myopic errors. These procedures require radial cutting of the cornea about the periphery of the graft which weakens the cornea so that pressure from fluids below the incisions pushes up under the cuts and flattens the curvature of the cornea. This flattening of the cornea results in refractive errors to the eye not compensated for by the graft. Suturing in these operations also causes radial asymmetry of the cornea which consequently promotes astigmatic error in this regard. Sutures also cause scarring of the corneal tissue, which scar tissue loses its transparency. Surgical correction of astigmatism is accomplished by asymmetrically altering the corneal curvatures. The effect of a peripheral distorting force may be easily visualized by imagining an inflated balloon with a spherical surface being compressed between the palms of the hands. Because the volume of air in the balloon is constant, the surface area remains constant. The previously spherical anterior surface is distorted meridianally as a result of compressing the diameter between the hands so that the curvature changes without changing the circumference of the surface. The meridian passing over the balloon between the extended fingers steepens, while the uncompressed meridian at right angles thereto flattens as its diameter lengthens in proportion to the shortening of the compressed diameter. This demonstrates the effect that may result from slight variations in the symmetrical patterns or intentional asymmetrical patterns attempted to be accomplished during surgical procedures and attendance suturing. It is thus seen that present procedures in keratorefractive techniques are best limited to situations where other more standard corrective practices are found in effective. It is readily seen that the limiting factors in such surgical techniques is the gross complexity involved not only with multiple incisions in corneal tissue for affecting the procedures but also complex suturing patterns, resulting in gross restructuring of the eye. The eye is thus faced with a difficult job of adjusting to this trauma.

Over the past few years developments have been made in the use of lasers as a means to reshape the cornea in an attempt to get rid of refractive errors. In these processes, pulsed lasers remove tissue from the cornea, the most common type being an Exemer laser. The fundamental effect of such a laser on tissue is a photochemical one, the breaking of molecular bonds with so much energy that the tissue fragments fly from the surface at supersonic speeds, leaving behind a discreet space. The process has been designated as ablative photodecomposition or photoablation.

The use of Exemer lasers require delivery of the beam to the eye in a controlled manner requiring that the homogenous beam be appropriately managed and focused because the optical elements must withstand the high energy photons, and because the beam must be shaped to a non-uniform configuration to create the new non-uniform optical surface of the cornea. Such delivery system contains multiple components including lenses to expand or focus the beam, mirrors to direct the beam, modulators to homogenize the beam, masks to shape the beam, and detectors to measure the intensity and configuration of the beam. Current models range from a simple collection of lenses and masks to complex robots with components that control not only the laser parameters but also the optical and mechanical components. Because the process is dealing with submicron (less than 0.00001 of a meter) accuracy, great demands are placed upon such systems for stability, even though the interaction of the laser and tissue lasts only microseconds.

Using the system requires exquisite technical and biological control to modulate corneal wound healing.

Other concepts for correcting refractive error of the cornea are found in the following patents and publications:

| | |
|---|---|
| 4,526,171 | Schachar |
| 4,662,370 | Hoffman |
| 4,947,871 | Grieshaber |
| 4,750,491 | Kaufman, et al |

Microsurgery of the Cornea, J. Barraquer, et al (1984) Ediciones Scriba, S.A.

SUMMARY OF THE INVENTION

It is therefore an object of the present invention to provide a new and improved keratorefractive technique involving method and apparatus for changing the shape of the optical zone of the cornea to correct for the refractive error of hyperopia (far-sightedness) whereby a minimum disturbance is imposed on the eye system and the simplicity of the technique virtually eliminates the chance of error or further complications resulting from gross disturbances of the eye system.

With this and other objects in view, the present invention contemplates a method and apparatus for scraping, sculpting or scarifying the cornea to change its curvature for the purpose of correcting refractive error.

Another object of the invention is to provide mechanical apparatus capable of easily being used by a surgeon for scraping, sculpting or scarifying the cornea in order to correct for hyperopia which includes means to provide consistency in depth and configuration of the surface.

Specifically, the method objects of this invention involve the surgical reprofiling of the corneal portion of the eye to change the corneal radius and thus correct refractive errors. One such method includes the steps of creating a placido ring keratograph of a simulated cornea having the correct refractive qualities. Next, keratograph of the cornea to be corrected is created. The two keratographs are compared to determine the amount of refractive error, i.e., whether it would be hyperopia, myopia, or astigmatism. A profiling tool is constructed that includes at least one but preferrably a plurality of sharpened, knife-edge blades of shape sufficient to scrape or sculpt the cornea and thus change its corneal radius to that of the simulated cornea. The profiling tool is then positioned within a holding sleeve that is contiguously positioned upon said eye initially such that the blades will contact the cornea tangentially, i.e., at a single point. The profiling tool is then rotated or oscillated until the corneal radius has been corrected to that of the simulated cornea. The profiling tool includes means for making precise axial depth changes as needed during the operational procedures.

Another object of the invention is to provide a profiling tool that is capable of applying non-scraping pressure to an anterior visual axis center zone of the cornea to thereby cause the outer band of the cornea outside said center zone to contact sharpened knife edge blade or blades which will scrape said outer portion and thus change the curvature of the cornea to correct hyperopic refractive error.

Hyperopic correction requires a steepening of the corneal curvature. It is a primary object of this invention to accomplish such steepening by scraping an anterior surface zone or band of the cornea that extends outwardly beyond a diameter of about 1.5 mm centered about the visual axis of the cornea.

One specific form of apparatus used to achieve the objects of this invention includes a circular positioning ring for temporary attachment to the sclera portion of an eye which surrounds the cornea that is to be reprofiled. Ordinarily a vacuum applied to the positioning ring is not necessary, however, provision is made to apply a vacuum if needed. A plurality of positioning pins exist on the top side of the positioning ring. If needed, a vacuum means is provided for communication with the vacuum ring. A cylindrical holding sleeve includes means at the bottom of the holding sleeve to interconnect with the positioning pins of the circular positioning ring. Fine micrometer-like adjustment screw threads of a given pitch, e.g., about 40 threads per inch, are formed on the exterior portion of the holding sleeve. Threadably connected thereto is a guide sleeve having screw threads of the same pitch which are formed interiorly thereof for rotatable attachment with the holding sleeve. A profiling tool is adapted to be rotatably and axially received within the positioning ring, the holding sleeve, and the guide sleeve. A collar means existing on the profiling tool allows it to be rotatably supported upon the guide sleeve. A plurality of sharpened knife-edge blades at the bottom of the profiling tool are designed to be of a shape sufficient to scrape, sculpt or form the desired corrective curvature in the corneal portion. One form of the tool includes at its bottom center a pressure pad of non-abrasive, reduced friction material, e.g., TEFLON or other polymers. Outward therefrom are a plurality of curved sharpened knife-edge blades. The curvature of which is slightly greater than the curvature of the aforesaid anterior surface zone or band of the cornea. Another form of tool includes sharpened straight knife-edge blades as shown in said copending and related patents and applications wherein a center portion of each said blades is not sharpened or capable of non-scraping pressure against said center zone.

Another object of the invention is to provide a means to incise by scraping, sculpting, and/or scarifying the outer anterior surface of a cornea to reprofile same to correct for refractive error, and to do so with a minimum or no inflammation and with regrowth of the epithelium-like layers or lamina of the cornea in a minimum amount of time.

Another object is to achieve a reprofiled cornea, as set forth in the previous object, that will permit regrowth of the epithelium layer from unshaped areas of the cornea, without returning to the original curvature.

DETAILED DESCRIPTION OF THE PREFERRED EMBODIMENT

Before explaining the present invention in detail, it is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

Figures 1, 2:
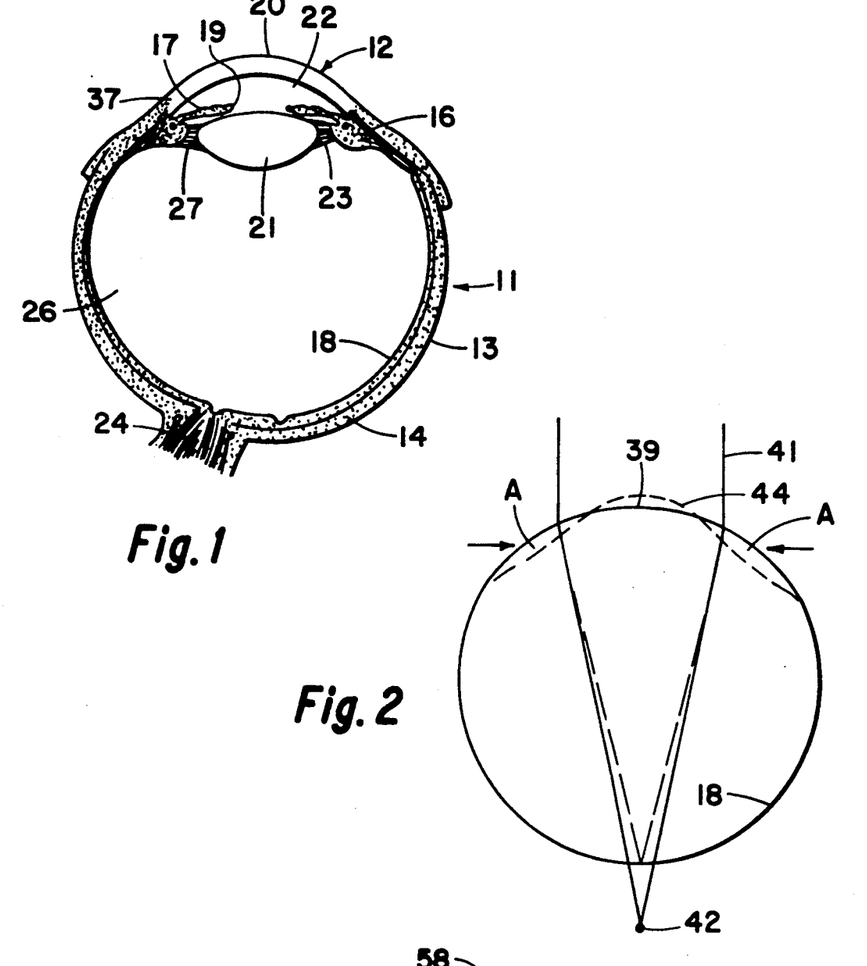
FIG. 1 is a schematic illustration of a horizontal section of the eye.
FIG. 2 is a schematic illustration of a hyperopic eye showing adjustment of the cornea to shorten the radius of curvature.

Referring first to FIG. 1 of the drawings, a horizontal section of the eye shows the globe of the eye resembling a sphere with an anterior bulged spherical portion 12 representing the cornea. Thus the eye is actually comprised of two somewhat modified spheres placed one in front of the other. The anterior of these two segments is the smaller more curved cornea.

The globe of the eye consists of three concentric coverings enclosing the various transparent media through which the light must pass before reaching the sensitive retina. The outermost covering is a fibrous protective portion, the posterior five-sixths of which is white and opaque and called the sclera 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 16 and iris 17. The choroid generally functions to maintain the retina 18. The ciliary muscle is involved in suspending the lens and accommodation of the lens. The iris is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina 18. It contracts also to accommodation, which serves to sharpen the focus by diminishing spherical aberration. The iris divides the space between the cornea 12 and the lens 21 into an anterior chamber 22 and posterior chamber 23. The innermost portion of covering is the retina 18, consisting of nerve elements which form the true receptive portion for visual impressions.

The retina 18 is a part of the brain arising as an outgrowth from the fore-brain, with the optic nerve 24 serving as a fibre tract connecting the retina part of the brain with the fore-brain. A layer of rods and cones, lying just beneath a pigmented epithelium on the anterior wall of the retina, serve as visual cells or photoreceptors which transform physical energy (light) into nerve impulses.

The vitreous 26 is a transparent gelatinous mass which fills the posterior four-fifths of the globe. At its sides it supports the ciliary body 16 and the retina 18. A frontal saucer-shaped depression houses the lens 21.

The lens 21 of the eye is a transparent bi-convex body of crystalline appearance placed between the iris 17 and vitreous 26. Its axial diameter varies markedly with accommodation. A ciliary zonule 27, consisting of transparent fibers passing between the ciliary body 16 and lens 21 serves to hold the lens in position and enable the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards it periphery. Most of the refraction of the eye takes place on the surface of the cornea.

Referring next to the FIG. 2 schematic of the drawings, the globe of an eye is shown having a cornea 12 with a normal curvature represented by the solid line 39. If parallel rays of light 41 pass through the corneal surface 39 of FIG. 2, they are refracted by the corneal surfaces to converse eventually near the retina 18 of the eye. The diagram of FIG. 2 discounts, for the purposes of this discussion, the refractive effect of the lens or other portions of the eye. The eye depicted in FIG. 2 is hyperopic and thus the rays of light 41 are refracted to converge at point 42 behind the retina. If a peripheral band of pressure is applied inwardly at the chord 43 of the cornea, the walls of the cornea are caused to steepen. This is because the volume of fluids within the anterior chamber 22 remains constant, thus the anterior portion of the cornea, including the optical zone (inner third of the cornea) steepens in slope to form a curvature (shown in exaggeration) following the dotted line 44. The rays of light 41 are then refracted from the steeper surface 44 at a greater angle to direct the refracted rays into focus at shorter distance, such as directly on the retina 18.

Figure 3:
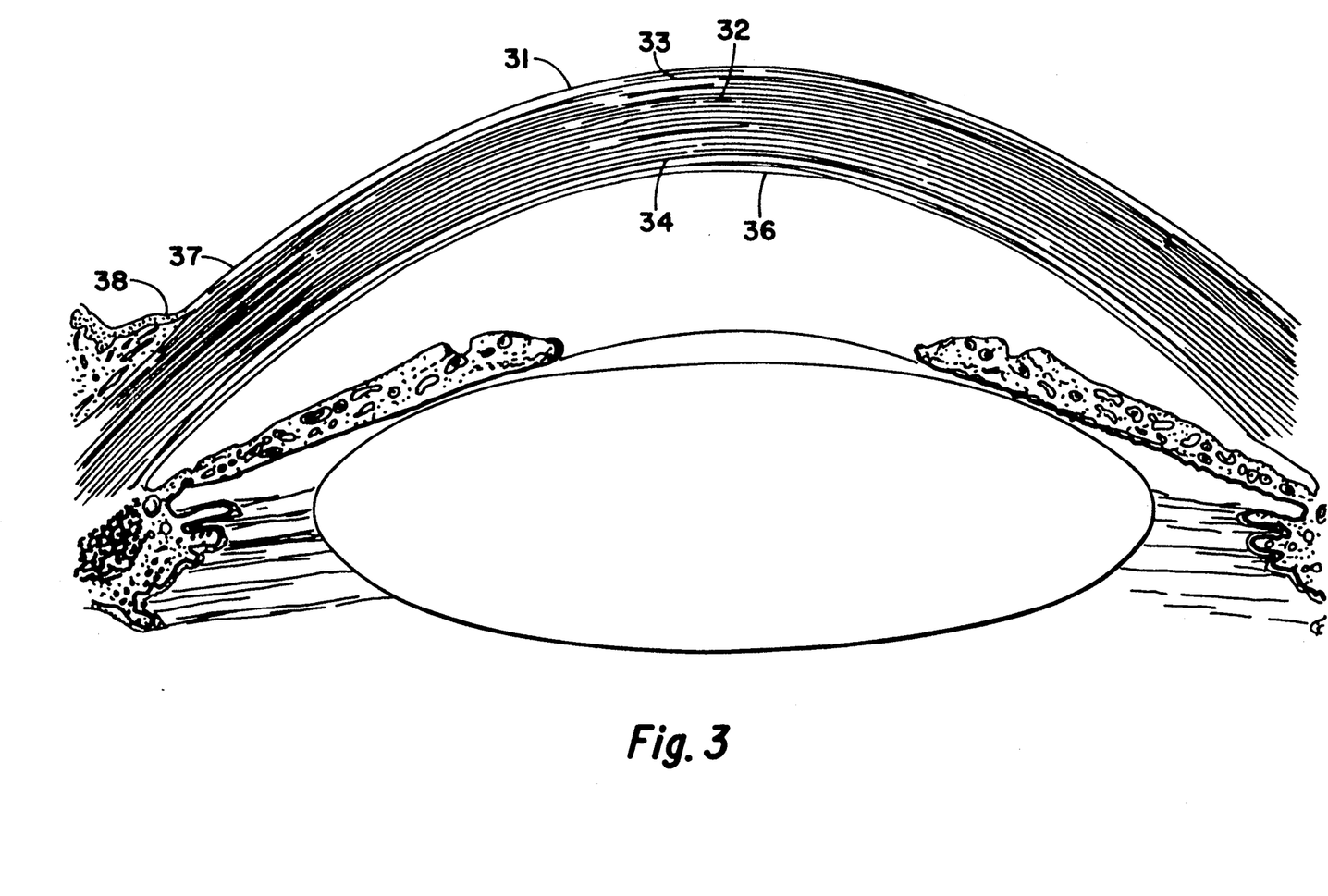
FIG. 3 is a detailed schematic illustration of a horizontal section of the frontal portion of an eye showing the various layers of the cornea.

Referring now to FIG. 3, a more detailed drawing of the anterior portion of the globe shows the various layers of the cornea comprising an epithelium 31. Epithelial cells on the surface thereof function to maintain transparency of the cornea. These epithelial cells are rich in glycogen, enzymes and acetylcholine and their activity regulates the corneal corpuscles and controls the transport of water and electrolytes through the lamellae of the stroma 32 of the cornea.

An anterior limiting lamina 33, referred to as Bowman's membrane, is positioned between the epithelium 31 and the substantia propria or stroma 32 of the cornea. The stroma is comprised of lamella having bands of fibrils parallel to each other and crossing the whole of the cornea. While most of the fibrous bands are parallel to the surface, some are oblique, especially anteriorly. The fibrous bands within alternate lamella are at a near right angle to bands in the adjacent lamella. A posterior limiting lamina 34 is referred to as Descemet's membrane. It is a strong membrane sharply defined from the stroma and resistant to pathological processes of the cornea.

The endothelium 36 is the most posterior layer of the cornea and consists of a single layer of cells. The limbus 37 is the transition zone between the conjunctiva 38 and sclera 13 on the one hand and the cornea 12 on the other.

Figure 4:
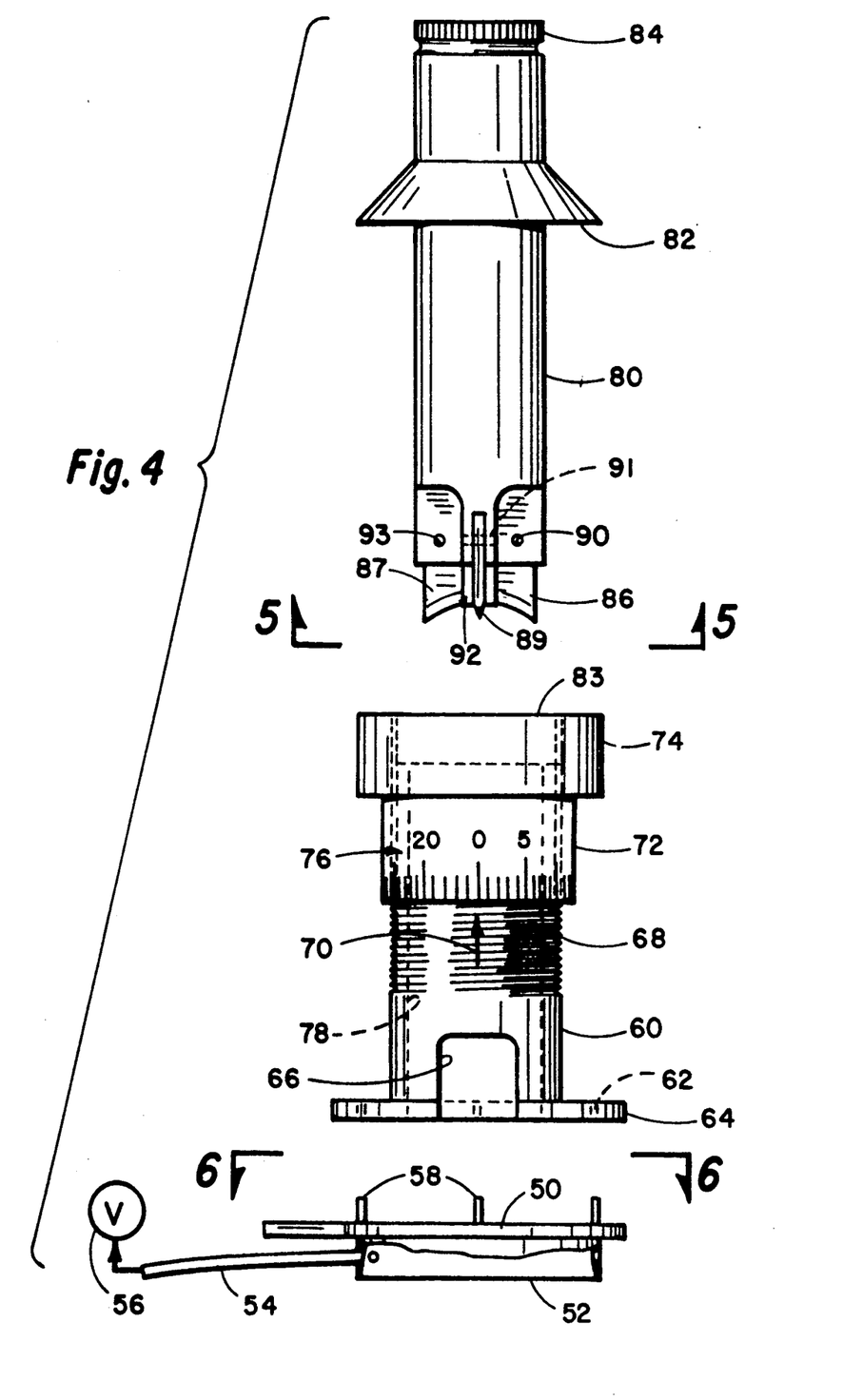
FIG. 4 is an exploded view showing the basic components of the apparatus of this invention.
Figure 5:
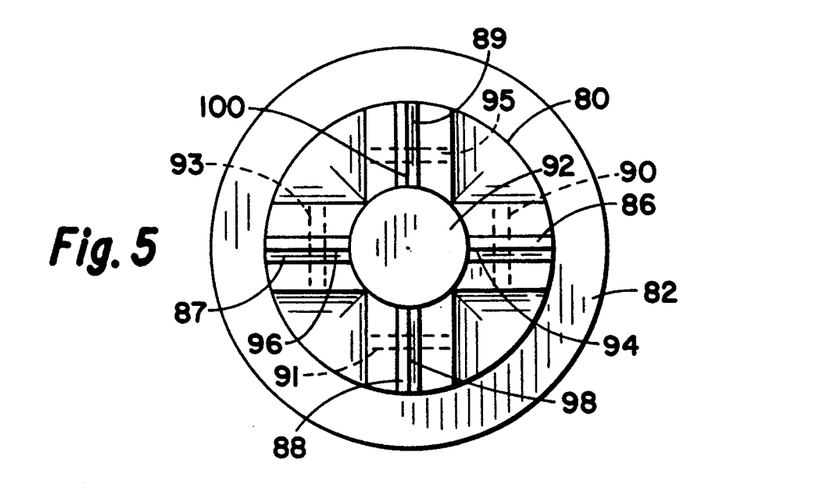
FIG. 5 is a bottom end elevational view of the profiling tool taken along the line 5—5 of FIG. 4.
Figure 6:
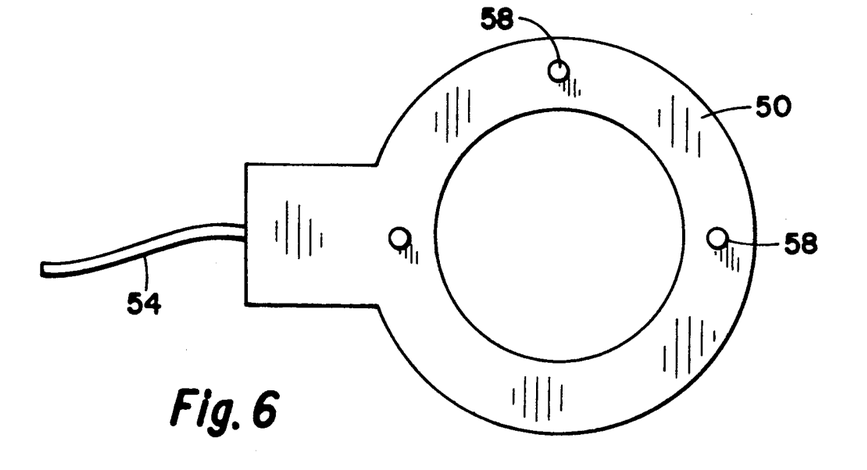
FIG. 6 is a top elevational view of the positioning ring of the invention.

Referring now to FIG. 4 wherein the assembly of the basic parts of the apparatus are shown in an exploded view. These parts comprise a cylindrical positioning ring 50 having a resilient ring 52 extending from the bottom side of the positioning ring for contact with the eye of the patient being treated (See also FIG. 9). If needed, a vacuum hose 54 provides communication from the inside of the resilient ring 52 and a vacuum pump source means 56 as a means to retain or affix the assembled parts upon the eye for surgical procedures herein described and to remove scarified portion of the cornea. Low vacuum of the order of not more than 8" Hg may be used. A plurality of positioning pins 58 are provided on the top side of the positioning ring to receive the cylindrical holding sleeve 60, the pins being adapted to be received through openings 62 in the flange portion 64. A visual inspection opening 66 is provided for use by the surgeon. The exterior of the cylindrical holding sleeve 60 includes a plurality of screw threads 68 along its length, the threads being a very fine micrometer-like thread, e.g., of a pitch equal to 40 threads per inch. An indicia or marker 70 is provided in the body of the cylindrical holding sleeve so as to provide a visual measuring point for the surgeon relative to the rotatable position of guide sleeve 72 which includes interior micrometer-like threads to match threads 68 of the cylindrical holding sleeve. The guide sleeve includes an outer knob portion 74 and indicia generally designated by the numeral 76, e.g. millimeter or micrometer like measurement markings on the lower portion of the guide sleeve. The interior 78 of the cylindrical holding sleeve is adapted to rotatably receive a profiling tool 80. The profiling tool includes a collar 82 which is adapted to rest upon the top surface 83 of the guide sleeve 72 for axial movement upwardly or downwardly therewith. The top end of the profiling tool can include a knurled portion 84 for finger rotation and/or oscillation of the tool 80 by the surgeon. At the bottom of the profiling tool are a plurality, e.g. four (4) surgically sharp curved knife-edge blades 86, 87, 88 and 89 which are radially or transversely retained within the body of the profiling tool 80 by pins 90, 91, 93 and 95. The blades 87, 88 and 89 are retained transverse to the longitudinal axis of the profiling tool 80. The blades as used in the invention are of surgical steel. Centrally located adjacent the blades 86 and 88 is a pressure pad 92 constructed of a non-abrasive reduced friction material, such as NYLON, TEFLON. The purpose of pressure pad is two-fold, i.e., prevent scraping in the central area of the cornea, and to cause pressure to be placed upon the center forcing that outer band of the cornea (A of FIG. 2) to bulge outward into contact with the blades, because of the liquid pressure in the eye. As will be described herein in greater detail, the blades are adapted to contact the outer anterior zone or band of the cornea in order to shorten the effective radius thereof, that is, the blades will be essentially adapted to contact and scrape the band in area A as shown in FIG. 2.

Figure 7:
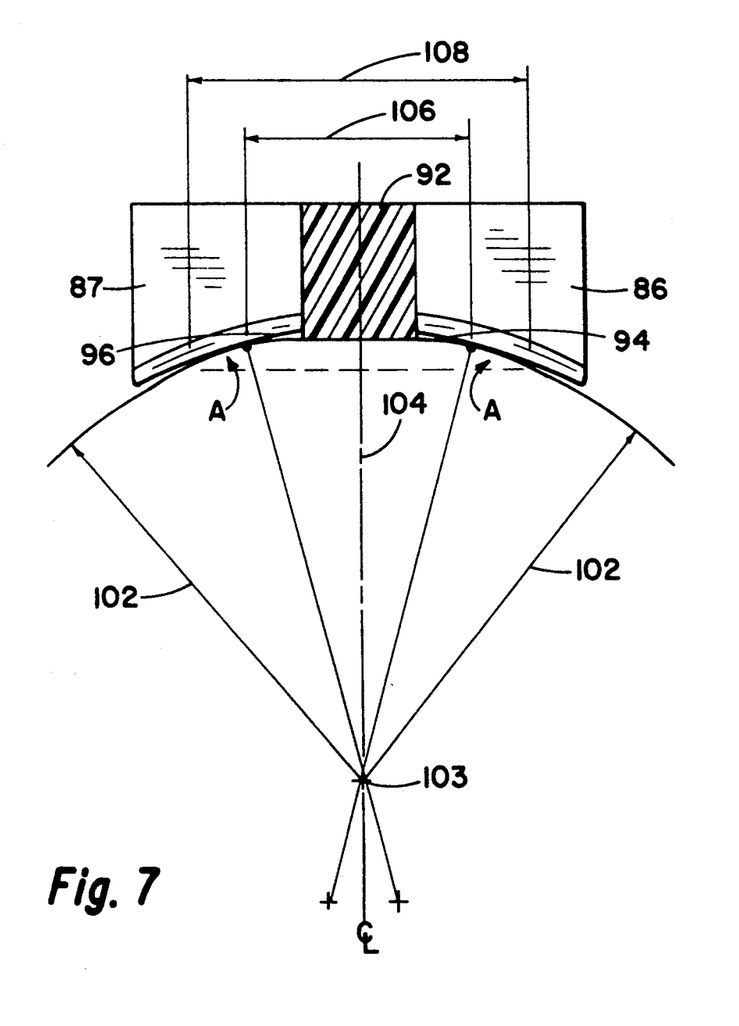
FIG. 7 is a partial sectional and diagrammatic view of the profiling tool apparatus of the invention relative to its initial position on a patients cornea.

Not to be considered as limiting but by way of example, a typical profiling tool 80 at the working end is 10 mm in diameter with a central pressure pad 92 2 mm in diameter. The pad 92, as shown in FIG. 7 extends slightly below, about 0.1 mm, the inner ends 94, 96, 98 and 100 of the respective four (4) blades 86, 87, 88 and 89. The radius of the blade is to be slightly larger than the corneal radius. For example, referring to FIG. 7, where the radius 102 from the corneal center 103 is 7.9 mm, the curvature of the blade would be 10 mm. As such the concentric circle, relative to the visual axis 104, of first tangential contact of the blades with the cornea occurs at a co-axial diameter 106 of about 4 mm while the circle 108 of final contact occurs at a diameter of 6 mm.

Figures 8, 9, 10:
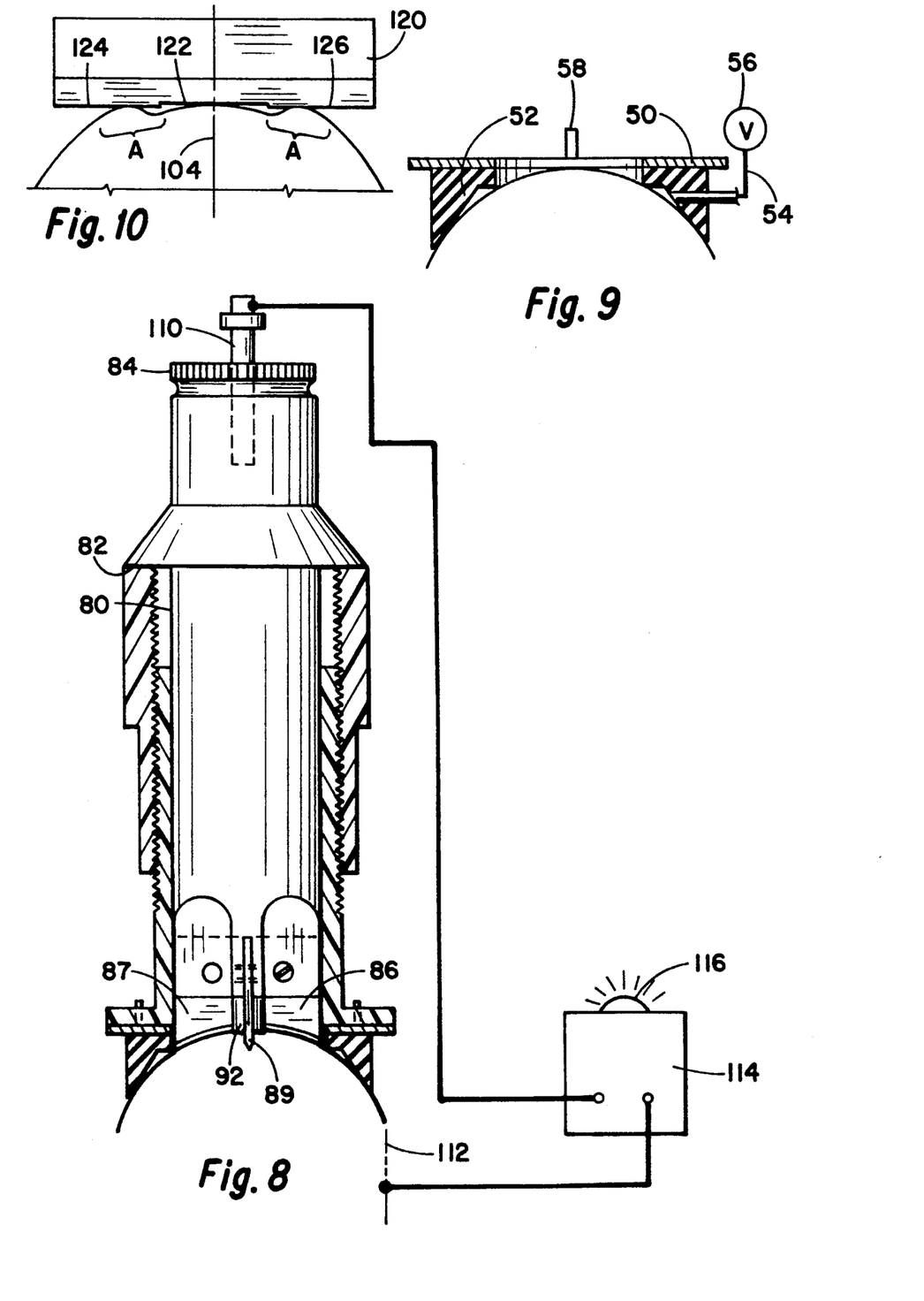
FIG. 8 is an assembly view of the apparatus of the invention with an electrical indicating means.
FIG. 9 is a sectional view of the positioning ring on an eye.
FIG. 10 is a partial/diagrammatic view of an alternate embodiment of the invention.

Referring to FIG. 10 a modified embodiment of this invention is described. Instead of a curved blade, in some instances one or more intersecting straight blades 120 comprise a non-sharpened center zone portion 122 which in this embodiment is above the sharpened edges 124 and 126 less than 0.001". The purpose of the center zone 122 is to apply non-scraping pressure against the center zone, i.e., about 2 mm in diameter causing the outer band A of the cornea to bulge against the scraping blades 124 and 126.

OPERATION

The operation of the apparatus and methods of surgery are accomplished by first taking optical measurements of the eye as to what shape the cornea should have in order for that eye to operate in an optically correct manner, i.e., correct refractive errors. Typically, a keratograph photographic image using a placito-ring target is used. The photograph is of reflected light from the placed rings upon a standard spherical surface of the same size as the cornea in question, creating an image in the same manner as a topographic contour map. Subsequently, the topographic survey of the eye to be corrected is made for comparison purposes and to provide the surgeon with the necessary information for correcting the refractive errors. The patients eye is anesthetized by a topical anesthetic and placed in a prone position. Typically a videokeratoscope/comparator is oriented to provide immediate visual information to assist the surgeon. Once this occurs, then the operation will proceed by placing the positioning ring 50 over the eye. The size of this ring may vary for different operations but is preferably of size wherein the resilient ring 52 will rest upon the sclera portion of the eye concentric about the cornea relative to its center visual axis. Once the circular positioning ring 50 is in place and held there if necessary by vacuum from a source not shown via conduit 54, the cylindrical holding sleeve 60 is then positioned thereupon by the engagement of openings 62 with positioning pins 58. The profiling tool 80 is then inserted within the cylindrical holding sleeve 60 to a position where as shown in FIG. 7 the bottom arc of the knife-edge blades 86–89 will initially and tangentially contact the cornea. This contact can be determined electrically as described herein relative to FIG. 8. By rotating the guide sleeves 72 in incremental amounts as dictated by the caliper or measuring indicia means 70 and 76, the surgeon can continue to increase the axial depth of the scraping or sculpting operation. Corneal tissue can be removed in increments of about 0.25 of a diopter of refractive change. The scraping, scarifying or sculpting of the cornea occurs by manual, i.e, hand/finger rotation or oscillation of the profiling tool 80 although other mechanical or motor operated means capable of reproducing manual rotation are within the scope of this invention.

During the operation, the pad 92 rotates with, or, in one embodiment relative to the tool 80 and bears on the center of the cornea both as a protective means and as a means to apply pressure to the cornea. That is, as the pad 92 bears on the cornea a small circular bulge is formed which rises up between and outward toward the blades 86–89 and will be preferentially scraped as the tool is rotated without any scraping of the central portion of the cornea for at least the diameter of the pad 92, i.e., about 1 mm to 2 mm in diameter in the example described. As described heretofore the initial placement upon the eye makes contact at a tangential ring of about 2 mm from the visual axis or 4 mm in diameter, which is first scraped. As the tool is axially advanced the scraped band widens thus causing the inner diameter to become smaller while the outer diameter becomes larger until it is about 6 mm diameter. The limit of scraping is achieved when the inner scraped diameter reaches the center pad or in the example when the outer diameter is about 6 mm. When the tool is removed and eye returns to its normal shape the ring area that has been scraped has a changed radius which is shorter than the original radius by virtue of having scraped away the bulged ring caused by the central pressure pad 92. The concept requires measurements of the corneal radius in order that the proper blade radius will cause the initial tangential contact to be about a ring of 4 mm in diameter.

In one example, a hyperopic (far-sighted) eye had an initial radius of 7.9 mm and was steepened to 7.5 mm thus moving the focal point 42 of FIG. 2 to a point within the retina 18, thus correcting the refractive error. The scraping action occurs by the surgeon in incremental axial movements by rotating the guide sleeve 72 relative to the cylindrical holding sleeve 60 utilizing the incremental measuring indicia 76 relative to pointer or other indicia 70. Typically, the guide sleeve is graduated into 25 or 50 micrometer divisions to provide one hundredth millimeter adjustments for each marked division of rotation. Through use, the surgeon begins to decide the amount of downward movement needed to achieve the required changes in the cornea by the rotation and/or oscillation of the knives. The rotation for a period of a few seconds will result in removal of small amounts of corneal material from the cornea. The tool can be removed at the end of each increment and keratographic photographs or other measuring means used to determine if the refractive error has been corrected. Since the apparatus and the surgical methods deal with very small increments of movement in the corneal reprofiling process, it is essential that the first contact setting be precise and accurate. Many times this can be done by visual means by the surgeon and in other instances electrical detecting means can be provided between the cornea and the tool blade to provide an exact setting of the tool which permits repeatable amounts of corneal removal. FIG. 8 describes this procedure.

A first contact electrode 110 is removably connected with the conductive tool 80. A second electrode is grounded to the patient at 112. The leads are connected to a low voltage power source 114 including an alarm or indicator lamp 116. Once the blade touches the cornea, the light or other alarm will go on which provides the initial contact point from which downward movement measurements begin. Typically a predetermined amount of corneal material is set into the tool by rotating the guide tool 72 downwardly. The rotation or oscillation of the profiling tool 80 then begins to change the contour of the cornea. Measurements are then taken to determine if more corneal material removal is necessary. If so, a new depth is set, and the process is repeated. The profiling tool is designed to be removed and replaced without changing the depth setting of the sleeve 72. Typically the amount of depth removal is about two thousandths of an inch (0.002"). Many times it is necessary to operate in several cycles with measurements being taken after each cycle. A nomogram used with a computer generated set of curves of the cornea before and after each contouring procedure permits the surgeon to constantly monitor the amount of removal of the epithelium layer and/or in some cases portions of Bowman's layer. It has been found that regrowth of the epithelium will occur over the surface of the scraped portion in a period of 24 to 48 hours and usually less than 72 hours. The epithelium will return and regrow to its same thickness and clarity but now with a changed radius.

What is claimed is:

1. A method of correcting hyperopic refractive error in an eye having a cornea with a visual axis and of given radius comprising the steps of:
   providing a tool having a central pressure pad and a plurality of sharpened knife-edge blades that extend outward from said central pressure pad, said blades curved at a radius larger than said radius of said cornea;
   initially positioning said tool co-axially with said visual axis and against said cornea such that said knife-edge blades are tangential to and against that portion of said cornea along a ring that is greater in diameter than said central pressure pad; and
   rotating or oscillating said knife edges about said visual axis so as to scrape said cornea with said knife edges until said refractive error has been substantially corrected.

2. A method of correcting hyperopic refractive error in an eye having a cornea with a visual axis and of given radius comprising the steps of:
   providing a tool having a plurality of sharpened knife-edge blades that extend outward from a central pressure pad, said blades curved at a radius larger than said radius of said cornea;
   initially positioning said tool co-axially with said visual axis and applying pressure against said cornea with said central pressure pad such that said knife-edge blades are tangential to and against that portion of said cornea along a ring that is greater in diameter than said pressure pad; and
   manually rotating or oscillating said knife edge about said visual axis so as to scrape said cornea with said knife edges until said refractive error has been substantially corrected.

3. A method of correcting hyperopic refractive error in an eye having a cornea with a visual axis and of given radius comprising the steps of:
   providing a tool having a plurality of sharpened knife-edge blades that extend outward from a central pressure pad, said blades curved at a radius larger than said radius of said cornea;
   initially positioning said tool co-axially with said visual axis such that said knife-edge blades are tangential to and against said cornea along a ring that is greater in diameter than said pressure pad;
   rotating or oscillating said knife edge about said visual axis so as to scrape said cornea with said knife edges until said refractive error has been substantially corrected; and
   axially advancing said blade incrementally against said cornea until said refractive error has been corrected.

4. The method of claim 1 wherein said pressure pad is 2 mm in diameter and said ring is 4 mm in diameter.

5. The method of claim 2 wherein said pressure pad is 2 mm in diameter and said ring is 4 mm in diameter.

6. The method of claim 3 wherein said pressure pad is 2 mm in diameter and said ring is 4 mm in diameter.

7. A method of reprofiling the corneal portion of an eye to change the corneal radius and thus correct hyperopic refractive errors, comprising the steps of:
determining the amount of said refractive error;
creating a visual topographic keratograph of said corneal portion of said eye;
comparing said visual keratograph with a visual display means showing the corneal radius as corrected for said refractive error;
providing a tool having a plurality of sharpened knife-edge blades that extend outward from a central pressure pad, said blades curved at a radius larger than said radius of said cornea;
initially positioning said tool co-axially with said visual axis such that said knife-edge blades are tangential to and against said cornea along a ring that is greater in diameter than said pressure pad;
rotating or oscillating said knife edge about said visual axis so as to scrape said cornea with said knife edges until said refractive error has been substantially corrected; and
monitoring said keratograph until said refractive error has been substantially corrected.

8. A method of correcting hyperopic refractive error in an eye having a cornea defined anteriorly in the cornea by essentially an epithelium layer and a stroma portion comprising the steps of:
providing a tool having a plurality of sharpened knife-edge blades that extend outward from a central pressure pad, said blades curved at a radius larger than said radius of said cornea;
initially positioning said tool co-axially with said visual axis such that said knife-edge blades are tangential to and against said cornea along a ring that is greater in diameter than said pressure pad; and
rotating or oscillating said knife edge about said visual axis while simultaneously pressing and advancing said blades in controlled axial incremental amounts against said corneal epithelium layer so as to scrape said cornea with said knife edge until said refractive error is substantially corrected.

9. A method of correcting for hyperopic refractive error in an eye defined by a cornea with a visual axis and of a given radius comprising the steps of:
rotating or oscillating at least one knife-edge blade of curvature greater than the radius of said cornea against that portion of the cornea that is within a band whose upper ring is of radius greater than 1 mm from said visual axis and whose lower ring is of radius no greater than 3 mm from said visual axis, until said refractive error has been corrected.

10. The method of claim 9 including the step of advancing said blade incrementally axially along said visual axis.

11. A method of correcting for hyperopic refractive error in an eye defined by a cornea with a visual axis and of a given radius comprising the steps of:
rotating or oscillating at least one knife-edge blade of curvature greater than the radius of said cornea against that portion of the cornea that is within a band that extends outward of a central area that is co-axial to said visual axis, until said refractive error has been corrected.

12. The method of claim 11 including the step of advancing said blade incrementally axially along said visual axis.

13. The method of claim 11 including the step of applying downward pressure to said central area during said rotating or oscillating.

14. The method of claim 13 including the step of advancing said blade incrementally axially along said visual axis.

15. A method of correcting hyperopic refractive error in an eye having a cornea with a visual axis and of given radius comprising the steps of:
providing a tool having a plurality of sharpened knife-edge blades that extend outward from a central axis, said blades having a central unsharpened portion and sharpened knife-edge blade that extends outward from said central unsharpened portion;
initially positioning said tool co-axially with said visual axis such that said knife-edge blades are tangential to said central unsharpened portion makes tangential contact with said cornea;
axially advancing said blades whereby said central unsharpened portion presses against a central zone of said cornea to thereby force that portion of said cornea outside said central zone into contact with said sharpened knife-edge blade; and
rotating or oscillating said knife edge about said visual axis so as to scrape said cornea with said knife edges until said refractive error has been substantially corrected.

16. Apparatus for surgically reprofiling the corneal portion of an eye to a desired corneal radius and thus correct hyperopic refractive errors, said cornea of a given radius and having a visual axis, comprising:
a profiling tool, said tool having a central pressure pad, at least one sharpened knife-edge blade that extends radially outward from said central pressure pad, said blade having a concave curve of a radius no smaller than said radius of the cornea; and
means to rotate or oscillate said profiling tool so as to scrape said cornea about the visual axis.

17. Apparatus of claim 16 including indexing means to provide indication of the axial location of said profiling tool relative to said cornea.

18. Apparatus for surgically reprofiling the corneal portion of an eye of a human to change the corneal radius and thus correct hyperopic refractive errors, said cornea of a given radius and a defined visual axis, comprising
a cylindrical positioning ring having resilient vacuum ring means on its bottom side for temporary attachment to a portion of the eye and surrounding the cornea to be reprofiled so as to be co-axial with the visual axis, positioning pins at a top side of said positioning ring, and vacuum means communicating with said vacuum ring means;
a holding sleeve, means at the bottom of said holding sleeve to interconnect with said positioning pins, screw threads of a given pitch formed on an exterior portion of said holding sleeve;
a guide sleeve having screw threads of said given pitch formed interiorly thereof for rotatable attachment with said holding sleeve;
a profiling tool, said profiling tool having a central pressure pad and adapted to be rotatably received co-axially with the visual axis within said positioning ring, said holding sleeve and said guide sleeve, a collar means on said profiling tool to rotatably support said profiling tool upon said guide sleeve, said profiling tool including said central pressure pad, a plurality of sharpened knife-edge blades at the bottom of said profiling tool of shape to sculpt the desired corrective curvature in the cornea, said blades extending radially outward from said central pressure pad, said blades curved at a radius larger than said radius of the cornea.

19. Apparatus of claim 17 wherein said holding sleeve is substantially transparent.

20. Apparatus of claim 17 wherein said pitch of said screw threads is between 35 to 50 threads per inch.

21. Apparatus of claim 19 wherein said pitch of said screw threads is 40 threads per inch.

22. Apparatus of claim 20 wherein said holding sleeve and said guide sleeve includes micrometer indexing means for measuring the axial movement of said profiling tool.

23. Apparatus of claim 18 including a first electrical contact connected to said profiling tool, a second electrical contact connected to said human, and an electrical power circuit means connecting said first and second contacts with a visual and/or audible indicator means.

24. Apparatus of claim 18 wherein said profiling tool includes frictional means releasably engageable with the inner periphery of said holding sleeve.

25. Apparatus for surgically reprofiling the corneal portion of an eye to correct hyperopic refractive error, comprising:
- a positioning ring having means to be temporarily attached to and surround the eye relative to a visual axis of the cornea to be reprofiled;
- a holding sleeve having means at its bottom to be retained by the positioning ring, a guide sleeve rotatably connected to the holding sleeve;
- a contouring tool adapted to be received within the holding sleeve and supported by the guide sleeve, the contouring tool comprised of means, at its bottom end, to scrape a portion of the cornea that is within a band whose upper anterior ring is of radius greater than 1 mm from said visual axis and whose lower ring is of radius no greater than 3 mm from said visual axis.

26. Apparatus for surgically reprofiling the corneal portion of an eye to a desired corneal radius and thus correct hyperopic refractive errors, said cornea of a given radius and having a visual axis, comprising:
- a profiling tool, said tool having a central portion, at least one sharpened knife-edge blade that begins at the periphery of said central portion and extends outward from said central portion; and
- means to rotate or oscillate said profiling tool so as to scrape said cornea about the visual axis.

27. Apparatus of claim 26 wherein said knife-edge blade extends downward and outward from said central portion.

28. Apparatus of claim 27 wherein said knife-edge blade is a concave curve of radius larger than said given radius of said cornea.

29. Apparatus of claim 27 wherein said knife-edge blade is straight.

30. A method of correcting hyperopic refractive error in an eye having a cornea with a visual axis and of given radius comprising the steps of:
- providing a tool having at least one sharpened knife-edge blade that extends outward from a central pressure pad, said blade curved at a radius larger than said radius of said cornea;
- initially positioning and maintaining said tool co-axially with said visual axis with said central pressure pad touching said cornea;
- axially advancing said tool whereby pressure of said central pressure pad forces that portion of said cornea outside said central pressure pad into contact with said sharpened knife-edge blade; and
- rotating or oscillating said knife-edge blade until said refractive error has been substantially corrected.

31. The method of claim 30 including the step of advancing said blade incrementally axially along said visual axis.

* * * * *